United States Patent [19]

Major et al.

[11] Patent Number: 5,690,927
[45] Date of Patent: Nov. 25, 1997

[54] USE OF NEURO-GLIAL FETAL CELL LINES FOR TRANSPLANTATION THERAPY

[75] Inventors: Eugene O. Major, Oakton, Va.; Carlo S. Tornatore, University Park, Md.; Kris Bankiewicz, Walnut Creek, Calif.

[73] Assignee: The United States of America as represented by the Department of Health and Human Services, Washington, D.C.

[21] Appl. No.: 459,136

[22] Filed: Jun. 2, 1995

Related U.S. Application Data

[63] Continuation of Ser. No. 46,527, Apr. 13, 1993, abandoned.
[51] Int. Cl.$^6$ .................................................... C12N 5/10
[52] U.S. Cl. .................. 424/93.21; 424/93.2; 424/93.7; 424/570; 424/582; 435/240.2

[58] Field of Search .................... 424/93.2, 93.21, 424/93.7, 570, 582; 435/240.2

[56] References Cited

FOREIGN PATENT DOCUMENTS 9106631  5/1991  WIPO .................................. 424/570

*Primary Examiner*—Jean C. Witz
*Attorney, Agent, or Firm*—Cushman Darby & Cushman IP Group of Pillsbury Madison & Sutro LLP

[57] ABSTRACT

Human fetal neuro-derived cell lines are implanted into host tissues. The methods allow for treatment of a variety of neurological disorders and other diseases. A preferred cell line is SVG.

21 Claims, 5 Drawing Sheets

USE OF NEURO-GLIAL FETAL CELL LINES FOR TRANSPLANTATION THERAPY

This is a Continuation of application Ser. No. 08/046,527 filed Apr. 13, 1993, now abandoned.

BACKGROUND OF THE INVENTION

The present invention relates generally to methods for treating a host by implanting genetically unrelated cells in the host. More particularly, the present invention provides methods of treating a host by implantation of immortalized human fetal neuro-derived cells.

Organ transplantation has become a successful and widely practiced means of treating a variety of diseases. Cardiac, renal, and even liver transplants are almost routine in many medical centers. Unfortunately, disorders of many organs are not amenable to treatment with whole organ transplants. For example, lesions of the central nervous system may not be treated by whole organ transplants to replace damaged tissue.

Because replacement of injured tissue by whole organ transplant therapy is not possible for many diseases, or even for all patients having appropriate diseases, attempts have been made to develop methods of transplanting cells. Sun et al., *Biomat., Art. Cells, Art. Org.*, 15:483–496 (1987). Parenchymal lesions which result in a deficiency of a biologically active compound may be treated by transplanting isolated cells or cell clusters that secrete the biologically active compound. For example, diabetic animals have been successfully treated by implantation of islets of Langerhans separated from donor pancreases. Noel et al., *Metabolism*, 31:184 (1982).

Cell transplant therapy is particularly appealing for treatment of neurological diseases. Solid tissue transplantation is especially inappropriate for neurological diseases for several reasons. Open surgical exposure of the brain, as required for solid tissue transplantation, can cause irreparable damage to nervous system pathways resulting in clinical neurological deficits. Also, neurological function often depends on complex intercellular connections which can not be surgically established. Further, cells of the central nervous system are exquisitely sensitive to anoxia and nutrient deprivation. Rapid vascularization of solid tissue transplants is critical as cells in the interior of solid tissue transplants often lack sufficient perfusion to maintain viability. Stenevi et al., *Brain Res.*, 114:1–20 (1976).

One common neurological syndrome, Parkinsonism has been the object of attempts at cell transplant therapy. Bj örklund et al., *Brain Res.*, 177:555–560 (1979); Lindvall et al., *Science*, 247:574–577 (1990); Freed, *Restor. Neurol. Neurosci.*, 3:109–134 (1991). Parkinsonism is caused by a loss of dopamine-producing neurons in the substantia nigra of the basal ganglia. Burns et al., *N. Engl. J. Med.*, 312:1418–1421 (1985); Wolff et al., *Neurobiology*, 86:9011–9014 (1989). Parkinson's disease, a disease of unknown etiology which is characterized by the clinical manifestations of Parkinsonism, is caused idiopathic destruction of these dopamine-producing neurons. Parkinsonism may be caused by a variety of drugs, e.g., antipsychotic agents, or chemical agents, e.g., 1-methyl-4-phenyl-1,2,3,6-tetrahydropyridine. Burns et al., *Proc. Natl. Acad. Sci. USA*, 80:4546–4550 (1983) and Bankiewicz et al., *Life Sci.*, 39:7–16 (1986).

Attempts have been made to reverse the clinical manifestations of experimentally-induced Parkinsonism by transplanting dopaminergic cells into the striatum of affected animals. Genetically modified fibroblasts (transfected with DNA encoding tyrosine hydroxylase) have been successfully transplanted into animals having lesions of dopaminergic pathways. Motor function and behavior of the animals improved following implantation of the dopamine producing fibroblasts. Wolff et al., *Proc. Natl. Acad. Sci. USA*, 86:9011–9014 (1989); Fisher et al., *Neuron*, 6:371–380 (1991). Graft survival may be enhanced, and hence clinical improvement prolonged, by transplantation of fetal tissue, as compared to cells obtained following birth. Gage and Fisher, *Neuron*, 6:1–12 (1991). Fresh fetal dopaminergic neurons have been transplanted into the caudate nucleus of monkeys following chemical injury to the nigrostriatal dopamine system. Following transplantation, the injury-induced behavioral deficits improved. Bankiewicz et al., *J. Neurosurg.*, 72:231–244 (1990) and Taylor et al., *Prog. Brain Res.*, 82:543–559 (1990).

Humans suffering from Parkinsonism have been treated by striatal implantation of dopaminergic neurons. Lindvall et al., *Arch. Neurol.*, 46:615–631 (1989); Widner et al., *New Engl. J. Med.*, 327:1556–1563 (1992). The transplanted cells were obtained from abortions. Prior to the abortions, the women were screened for antibodies to several disease causing viruses. Following surgery, the treated patients exhibited improvement of neurological function. The patients required maintenance immunosuppressive therapy, however.

Recent investigations indicate that trophic factors released from support cells of the central nervous system (e.g., astrocytes and oligodendrocytes) are critical to survival of neurons in cell culture. O'Malley et al., *Exp. Neurol.*, 112:40–48 (1991). Implanted fibroblasts that were genetically altered to express nerve growth factor have been shown to enhance survival of cholinergic neurons of the basal forebrain following injury to the fimbria-fornix which causes demise of acetylcholine neurons in the basal forebrain as seen in Alzheimer's disease. Rosenberg et al., *Science*, 242:1575–1577 (1988).

While previous attempts at cell transplant therapy for neurological disorders have provided encouraging results, several significant problems remain. The supply of fetal tissue for cellular transplants is quite limited. To ensure maximum viability, the fetal cells must be freshly harvested prior to transplantation. This requires coordinating the implantation procedure with elective abortions. Even then, fetal tissue has not been widely available in the United States. Also, the gestational age of the fetus from which cells are obtained influences graft survival. Gage and Fisher, supra. Obtaining fetal tissue of only certain gestational ages adds additional limitations to the availability of fetal cells for transplant. Further, ethical considerations make some potential transplant recipients reluctant to undergo the procedure when fresh fetal cells are implanted.

Because the fetal tissue is obtained from fresh abortuses, a significant risk of infectious contamination exists. Although women undergoing abortions which will supply fetal tissue are screened for a variety of infections, some infections, e.g. HIV, may not be clinically detectable and thus, not identified during the screening process. Therefore, if widely practiced, transplants of fresh fetal cells would likely cause many infectious sequelae.

Use of immortalized cell lines could overcome many of these difficulties of availability and infection. Only one immortalized human fetal neuro-derived cell line has been reported, however. Major et al., *Proc. Natl. Acad. Sci. USA*, 82:1257–1262 (1985) and U.S. Pat. No. 4,707,448. Further, immortalized cell lines, by their very nature, are predisposed to causing tumor formation following in vivo transplantation. Therefore, therapeutic intracerebral transplantations of immortalized cells carry a high risk of causing intracranial tumors, and even tumors having a benign histology may carry a poor prognosis when present within the calvarium.

Transplants of genetically unrelated cells carry the risk of immunological graft rejection and intracerebral inflammation. Widner and Brundin, *Brain Res. Rev.*, 13:287–324 (1988). All transplants of genetically unrelated cells carry this risk. Therefore, patients treated by intracerebral cell transplant have required long-term maintenance immunosuppression which, even in the absence of transplanted immortalized cells, carries a high risk of infectious and malignant complications. The transplantation of immortalized cells only magnifies the risk of these complications.

What is urgently needed in the art are methods of therapeutically implanting immortalized human fetal neuro-derived cells. Ideally, the methods would not result in tumor formation or elicit intense inflammation following transplantation. Desirably, the methods could employ cells derived from cell lines so that the risk of infectious contamination and limited cellular availability would be minimized. Quite surprisingly, the present invention fulfills these and other related needs.

SUMMARY OF THE INVENTION

The present invention provides methods for treating a host comprising implanting cells of an immortalized human neuro-derived fetal cell line into the host. Generally the cell line will be derived from human fetal astrocytes, such as the SVG cell line. The cells will often be implanted into the central nervous system of the host. The cells may be encapsulated by membranes which are impermeable to antibodies of the host.

In some embodiments of the invention, the cells may be transfected with a nucleic acid sequence encoding a peptide. The peptides will generally be enzymes, such as tyrosine hydroxylase, or growth factors, such as nerve growth factor. The peptide may also be a disease associated antigen. The cells may be implanted for purposes of treatment or prophylaxis. In some instances, the cells may be removed following implantation.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DESCRIPTION OF THE SPECIFIC EMBODIMENTS

Figure 1:
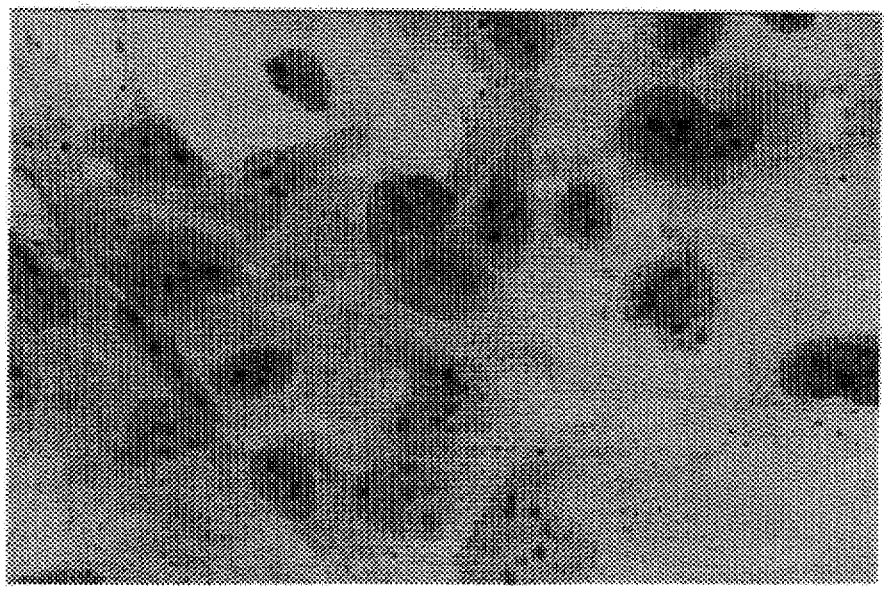
FIG. 1 demonstrates the morphology of SVG cells in vitro.

The present invention provides methods of treating a host by implanting immortalized human fetal cells derived from cells of the central nervous system. Graft rejection, intense intracerebral inflammation, and tumor formation have not been demonstrated following implantation of such cells into the central nervous system. Further, the cells have been shown to induce neuron migration and neurite extension. This demonstrates that the cells are functioning to produce trophic factors that stimulate neuronal responses.

Implantation of immortalized human fetal cells derived from cells of the central nervous system provides a means of treating many diseases. For example, Parkinson's disease may be treated by implantation of these cells into the basal ganglia of an affected host. The trophic factors produced by the implanted cells may inhibit dopaminergic neuron demise and even induce dopaminergic neuron regeneration. The increased population of dopaminergic neurons can provide clinical improvement of persons suffering from Parkinsonism. Alternatively, the implanted cells may be transfected with DNA encoding tyrosine hydroxylase. Expression of tyrosine hydroxylase by the implanted cells allows the cells to produce and secrete dopamine. Thus, the implanted cells may increase the dopamine concentration in the substantia nigra and limit or reverse the effect of dopaminergic neuron loss.

The methods of the present invention may also be used to treat neurological disorders such as Huntington's chorea, Alzheimer's disease, or multiple sclerosis. As immortalized human fetal neuro-derived cells are compatible with the central nervous system (CNS), these cells may be transfected with DNA sequences encoding physiologically active peptides and implanted in the CNS. For instance, in Huntington's chorea and amyotrophic lateral sclerosis the peptide may block excitatory neurotransmitters such as glutamate. In multiple sclerosis, the peptide may be a trophic stimulator of myelination, such as platelet derived growth factor or may be a ciliary trophic factor which may block oligodendrocyte demise. As these diseases are more generalized than local lesions, the cells may be implanted on a surface exposed to cerebrospinal fluid. Following expression and secretion, the peptide will be washed over the entire surface of the brain by the natural circulation of the cerebrospinal fluid. Suitable sites for implantation include the lateral ventricles, lumbar thecal region, and the like. In Alzheimer's disease, the cells may be transfected to produce nerve growth factor to support neurons of the basal forebrain as described by Rosenberg et al., *Science*, 242:1575–1578 (1988), incorporated herein by reference.

The methods of the present invention may also be employed to treat hosts by implantation of cells in extraneural sites. This embodiment of the present invention is particularly useful for prophylactic treatment of a host. Immortalized human fetal neuro-derived cells may be transfected with DNA encoding a disease-associated antigen, e.g. HIV gp120 polypeptides which encompass the principal neutralizing domain of HIV as described, e.g., in U.S. Pat. No. 5,166,050. The cells may then express and secrete the antigen encoded by the transfected DNA. The antigen may be continuously secreted by the implanted cells and elicit a strong immune response. Following an adequate time interval to fully immunize the host, the cells may be removed.

As used herein, "treating a host" includes prophylactic, palliative, and curative intervention in a disease process. The host may be any warm blooded mammal, such as humans, non-human primates, rodents, and the like.

A wide variety of diseases and syndromes may be treated by the methods of the present invention. Generally, the disease will be a neurological disease, such as Parkinsonism (including Parkinson's disease), Alzheimer's disease, Huntington's chorea, multiple sclerosis, amyotrophic lateral sclerosis, Gaucher's disease, Tay-Sachs disease, neuropathies, brain tumors, and the like. The methods of the present invention may also be employed in the treatment of non-neurological diseases. For example, the methods of the present invention may be used to immunize hosts against infectious diseases, such as viruses, bacteria, protozoa, and the like as described above. Immortalized human fetal neuro-derived cells may be transfected by DNA encoding physiologically active peptides or peptides which contain immunological epitopes. The methods of the present invention may be employed to implant the peptide producing cells and provide continuous in vivo delivery of peptides, such peptides, such as growth hormone, to the host.

The cells implanted by the methods of the present invention are immortalized human fetal neuro-derived cells. By "neuro-derived", it is meant that the prior to immortalization, the cells had a neurological cell phenotype or were an embryonic cell committed to differentiation to a neurological cell type. Neurological cell types include neurons, astrocytes, oligodendrocytes, choroid plexus epithelial cells, and the like.

Fetal cells may be collected following elective abortion. Women donating fetuses following abortion should be serologically screened for a variety of infectious diseases, including human immunodeficiency virus, hepatitis B virus, hepatitis C virus, cytomegalovirus, and herpes viruses Types 1 and 2. Fetuses will generally be 9–11 weeks of gestational age (7–9 weeks postconception). Fetal age may be confirmed by ultrasound. Fetuses may be extracted under ultrasound guidance to minimize fetal brain trauma.

Following extraction, the fetal brain is identified and dissected from the abortus. The cells may be prepared as follows. Brain tissue is aspirated through a 19 gauge needle and washed twice in Eagle's minimum essential media (E-MEM, Gibco, New York, N.Y.). Cells are plated on culture dishes treated with poly-D-lysine (0.1 mg/ml for 5 minutes). The cells are grown on E-MEM supplemented with 20% fetal bovine serum, 75 µg/ml streptomycin, 75 units/ml penicillin, 1% dextrose and 2 µg/ml fungizone (Gibco). Prior to immortalization the cells are incubated at 37° C. in a 5% $CO_2$ humidified environment. One of skill in the art will recognize that other methods for preparing cells may also be used.

Figure 2:
FIG. 2 illustrates immunoperoxidase staining of an antibody to SV40 T protein in SVG cells.

The cells to be implanted by the methods of the present invention can be immortalized by a variety of techniques. Typically, the cells will be immortalized as follows. The cell cultures will generally produce progenitor neuronal and glial cells, as well as neurons, as described by Major and Vacante, *J. Neuropath. and Exp. Neurol.*, 48:425–436 (1989), incorporated herein by reference. With regular refeeding, the brain cells will survive for several months but show little cell proliferation. Cells are transformed by transfection with a SV40 deletion mutant. The mutant DNA lacks an origin of replication (ori-) and can not multiply. Transfection of the DNA, however, will transform cells to unlimited growth potential as described by Gluzman, *Cell*, 23:175–182 (1981). After growing the fetal cell cultures for 3 weeks, the cells may be transfected with 100 µg/flask of plasmid DNA (pMK16) containing the SV40 ori- mutant using the calcium phosphate precipitation technique as described by Graham et al. *Virol.*, 52:456–467 (1973). Alternatively, the cells may be transfected by electroporation, or other well known techniques as described in Sambrook et al., *Molecular Cloning, A Laboratory Manual*, Cold Spring Harbor Press, 1988, incorporated herein by reference. Following transfection, the cultures are grown with weekly refeeding. After several weeks, proliferation of glial cells in separate areas of the plates becomes evident. The cells are then transferred by trypsinization (0.025%) to new cultures. Transformed cells may be identified by fluorescence antibody assays to detect the SV40 T protein which is expressed by transformed cells (FIG. 2). The cells are passaged every 10 days until an increase in the number of T protein positive cells is detected.

The transformed cells will display the phenotype of a continuous cell line. Specifically, the cells will grow to a high saturation density with a 18 hr generation time. The cells do not show the transformed phenotype or anchorage independent growth, however, which is characteristic of non-mutant SV40 transformed cells. The cell morphology is also not altered during the course of establishment of the cell line. Foci of cells are generally not detected. Particularly useful are cells from the SVG cell line deposited with the American Type Culture Collection, Rockville Md., (A.T.C.C. CRL 8621) which is described in U.S. Pat. No. 4,707,448, incorporated herein by reference (FIG. 1). Hereinafter by "SVG cells" or "SVG cell line", it is meant cells or a cell line derived from cell line A.T.C.C. CRL 8621. By derivatives is meant a subclone, replication, or genetically altered mutant of cell line A.T.C.C. CRL 8621.

Alternatively, the cells may be immortalized by other techniques which are well known in the art. For example, immortalization by Epstein-Barr virus may be employed, as described in U.S. Pat. No. 4,464,465, incorporated herein by reference. Epstein-Bart virus mutants which lack OriP and OriLyt origins of replication are particularly useful. Another useful method of immortalization is over-expression of a cellular gene for growth control such as c-myc as described by Bartlett et al., *Proc. Natl. Acad. Sci. USA*, 85:3255–3259 (1988), incorporated herein by reference. Generally, transformed cells suitable for implantation will be anchorage dependent, will not grow in soft agar, and will not exhibit foci formation.

Preferably, the cells will not elicit an immune response from the recipient host and thus, not require immunosuppression of the host following implantation. Conveniently, the cells, such as SVG cells, may not express MHC Class II molecules or MHC Class I molecules. Cells lacking expression of MHC Class I or Class II molecules may not elicit an immune response. Cells lacking expression of MHC Class II molecules may be derived from SVG cells or recombinantly constructed as described in U.S. Pat. No. 4,707,448, incorporated herein by reference. Functional MHC Class I or Class II molecule genes may also be removed by homologous recombination with vectors carrying non-functional MHC molecule sequences. The resulting cells would not produce functional MHC Class I or Class II molecules, respectively. Alternatively, expression of MHC Class I or Class II molecules may be suppressed in other cells. Suppression may be accomplished, e.g., by antisense nucleic acid sequences to block transcription or translation of nucleic acid sequences (DNA or RNA) encoding MHC Class I or Class II molecules, respectively. Expression vectors which constitutively express nucleic acid sequences complementary to conserved regions of MHC Class I or Class II molecule genes or RNA may be transfected into cells to suppress expression of the genes.

The histological origin of the transformed cells may then be determined. Characteristically, astroglial cells can be recognized by the presence of an intermediate filament composed of glial fibrillary acidic protein, GFAP. Oligodendroglial cells, on the other hand, are myelin producing cells and can be identified by their synthesis of a galactocerebroside, gal C, which is a component of myelin.

Following transformation, the cells will be prepared for implantation. The cells are suspended in a physiologically compatible carrier, such as cell culture medium (e.g., Eagle's minimal essential media) or phosphate buffered saline. Cell density is generally about $10^4$ to $10^7$ cells/ml. The cell suspension is gently rocked prior to implantation. The volume of cell suspension to be implanted will vary depending on the site of implantation, treatment goal, and cell density in the solution. For example, in the treatment of Parkinsonism, 5 µl to 60 µl of cell suspension will be administered in each injection. Several injections may be used in each host. Persons of skill will understand how to determine proper cell dosages.

The cells may be implanted within the parenchyma of the brain, in a space containing cerebrospinal fluid, such as the sub-arachnoid space or ventricles, or extraneurally. As used herein, the term "extraneurally" is intended to indicate regions of the host which are not within the central nervous system or peripheral nervous tissue, such as the celiac ganglion or sciatic nerve. "Extraneural" regions may contain peripheral nerves. "Central nervous system" is meant to include all structures within the dura mater.

When the cells are implanted into the brain, stereotaxic methods will generally be used as described in Leksell and Jernberg, *Acta Neurochir.*, 52:1–7 (1980) and Leksell et al., *J. Neurosurg.*, 66:626–629 (1987), both of which are incorporated herein by reference. Localization of target regions will generally include pre-implantation MRI as described in Leksell et al., *J. Neurol. Neurosurg. Psychiatry*, 48:14–18 (1985), incorporated herein by reference. Target coordinates will be determined from the pre-implantation MRI.

Prior to implantation, the viability of the cells may be assessed as described by Brundin et al., *Brain Res.*, 331:251–259 (1985), incorporated herein by reference. Briefly, sample aliquots of the cell suspension (1–4 µl) are mixed on a glass slide with 10 µl of a mixture of acridine orange and ethidium bromide (3.4 µg/ml of each component in 0.9% saline; Sigma). The suspension is transferred to a hemocytometer, and viable and non-viable cells were visually counted using a fluorescence microscope under epi-illumination at 390 nm. combined with white light trans-illumination to visualize the counting chamber grid. Acridine orange stains live nuclei green, whereas ethidium bromide will enter dead cells resulting in orange-red fluorescence. Cell suspensions should generally contain more than about 98% viable cells.

Injections will generally be made with sterilized 10 µl Hamilton syringes having 23–27 gauge needles. The syringe, loaded with cells, are mounted directly into the head of a stereotaxic frame. The injection needle is lowered to predetermined coordinates through small burr holes in the cranium. 40–50 µl of suspension are deposited at the rate of about 1–2 µl/min. and a further 2–5 min. are allowed for diffusion prior to slow retraction of the needle. Frequently, two separate deposits will be made, separated by 1–3 mm, along the same needle penetration, and up to 5 deposits scattered over the target area can readily be made in the same operation. The injection may be performed manually or by an infusion pump. At the completion of surgery following retraction of the needle, the host is removed from the frame and the wound is sutured. Prophylactic antibiotics or immunosuppressive therapy may be administered as needed.

For treatment of more generalized neurological disorders, cells may be transfected to express a therapeutic compound and implanted in the ventricles or lumbar theca. As the therapeutic compound is secreted by the cells, natural circulation of the cerebrospinal fluid washes the therapeutic compound throughout the central nervous system providing a means of generalized treatment. Implantation into the ventricles may be accomplished by an open procedure, such as described in Madrazo et al., *New Engl. J. Med.*, 316:831–834 (1987) or Penn et al., *Neurosurgery*, 22:999–1004 (1988), both of which are incorporated herein by reference. Implantation of cells into the lumbar theca is most conveniently accomplished by standard procedures similar to instillation of radiographic contrast media or antitumor medication via a lumbar puncture.

In some instances, it may be desirable to implant cells extraneurally according to the present invention. The cells may be implanted percutaneously through a needle or endoscope or by an open procedure. Persons of skill will readily appreciate the most appropriate method of implanting cells for particular applications.

The cells may be encapsulated by membranes prior to implantation. The encapsulation provides a barrier to the host's immune system and inhibits graft rejection and inflammation. Several methods of cell encapsulation may be employed. In some instances, cells will be individually encapsulated. In other instances, many cells will be encapsulated within the same membrane. When the cells will be removed following implantation, the relatively large size of a structure encapsulating many cells within a single membrane provides a convenient means for retrieval of the implanted cells. Several methods of cell encapsulation are well known in the art, such as described in European Patent Publication No. 301,777, or U.S. Pat. Nos. 4,353,888, 4,744, 933, 4,749,620, 4,814,274, 5,084,350, or 5,089,272, each of which is incorporated herein by reference.

One method of cell encapsulation is as follows. The transformed cells are mixed with sodium alginate (a polyanionic seaweed extract) and extruded into calcium chloride so as to form gel beads or droplets. The gel beads are incubated with a high molecular weight (MW 60–500×$10^3$) concentration (0.03–0.1% w/v) polyamino acid, such as poly-L-lysine, for a brief period of time (3–20 minutes) to form a membrane. The interior of the formed capsule is reliquified by treating with sodium citrate. The single membrane around the cells is highly permeable (MW cut-off 200–400×$10^3$). The single membrane capsule containing the cell is incubated in a saline solution for 1–3 hours to allow entrapped sodium alginate to diffuse out of the capsule and expand the capsule to an equilibrium state. The resulting alginate-poor capsule is reacted with a low molecular weight polyamino acid (MW 10–30×$10^3$) such a poly-L-lysine (PLL) or chitosan (deacetylated chitin; MW 240×$10^3$) to produce an interacted, less permeable membrane (MW cut-off 40–80×$10^3$). The dual membrane encapsulated cells are then cultured in E-MEM for two to three weeks as described above.

While reference has been made specifically to sodium alginate beads, it will be appreciated by those skilled in the art that any non-toxic water soluble substance that can be gelled to form a shape-retaining mass by a change in conditions in the medium in which it is placed may be employed. Such gelling material generally comprises several chemical moieties which are readily ionized to form anionic or cationic groups so that the surface layers can cross link to form a permanent membrane when exposed to oppositely charged polymers. Most polysaccharide gums, both natural and synthetic, can be cross-linked by polymers containing positively charged reactive groups such as amino groups. The cross-linking biocompatible polymers which may be reacted with the sodium alginate gum include polylysine and other polyamino acids. The degree of permeability of the membrane formed may be controlled by careful selection of a polyamino acid having the desired molecular weight. Poly-L-lysine (PLL) is the preferred polymeric material but others include chitosan and polyacrylate. Molecular weights typically vary from about $10^4$ to about $10^6$.

In some embodiments of the present invention, the implanted cells may be transfected with a DNA sequence encoding a peptide. The peptide may be a directly therapeutic compound, such as a movement inhibitor in the treatment of Huntington's chorea. Alternatively, the peptide may be an enzyme which catalyzes the production of a therapeutic compound, e.g., the DNA could encode tyrosine hydroxylase which catalyzes the synthesis of dopamine that is effective in the treatment of Parkinsonism. The DNA may also encode a trophic factor such as a nerve growth factor, an inhibitory growth factor, or a cytokine useful in the treatment of brain tumors.

Generally, the DNA sequence will be operably linked to a transcriptional promoter and a transcriptional terminator. The DNA sequence may also be linked to a transcriptional enhancer. Expression of the DNA in the implanted cells may be constitutive or inducible. A variety of expression vectors having these characteristics may carry the DNA for transfection of the cells, such as plasmid vectors pTK2, pHyg, and pRSVneo, simian virus 40 vectors, bovine papillomavirus vectors or Epstein-Barr virus vectors, as described in Sambrook et al., *Molecular Cloning, A Laboratory Manual*, Cold Spring Harbor Press, 1988, previously incorporated herein by reference. The vectors may be introduced into the cells by standard methods, such as electroporation, calcium phosphate-mediated transfection, polybrene transfection, and the like.

The following examples are offered by way of illustration, not by way of limitation.

EXAMPLE 1

This example describes preparation of SVG cells (A.T.C.C. CRL 8621) for implantation into rhesus monkeys. The cells were screened for infection with mycoplasma, HIV-1, Hepatitis B virus, virus, simian virus 40, Herpes simplex virus, cytomegalovirus, and JC virus.

SVG cells were grown to confluency. Cell growth was anchorage dependent. Foci formation did not occur and cell morphology was homogeneous. The cells were removed from tissue culture plates by digestion with 0.05% trypsin in 0.01M EDTA (Versene Buffer) in Hank's balanced salt solution. Cells were collected by centrifugation, washed 3 times and resuspended in phosphate buffered saline. Final cell density was $10^6$ cells/ml. The cell suspension was stored at 4° C. until transplantation.

EXAMPLE 2

This example describes implantation of SVG cells into the basal ganglia of six rhesus monkeys. The implantations were performed by stereotaxic methods without surgical complications.

The animals were initially anesthetized with ketamine and were maintained on isofluorine gas anesthesia during the course of the surgery. Animals were placed in the stereotaxic frame (Kopf) and the landmarks for implantation were established through the stereotactic coordinates. The superior sagittal sinus was exposed in order to establish the midline. Marks were placed on the cranium over the caudate and the putamen on both sides. The coordinates were as follows: AP was +24 mm in front of the 0. Lateral coordinates were 5 mm from the midline for the caudate nucleus, and 10 mm lateral from the midline for the putamen.

Five burr holes were made. One was made over the superior sagittal sinus, two over the caudates and two over the putamens. Two different implantation techniques were used.

1. 10 µl Hamilton syringes with 26 gauge needle or 50 µl Hamilton syringes with 23 gauge needles were used. on the right side of the brain SVG cells were transplanted. Using the syringes, two deposits were done in the putamen. One deposit was in the lateral putamen and the second was in the medial putamen. The needles were lowered at 18 mm from the cortex, then 10 µl of the cell suspension was implanted using the Kopf microinjector. After the first implantation the needle was removed 1 mm a minute for 3 mm and then the second injection of 10 µl of the cell suspension followed. After the second injection the needle was removed at 1 mm per minute. A second implantation was done in the opposite putamen at the same coordinates with the same technique.

After injecting the putamen, implantation into the caudate nucleus was performed with the same cell suspension. Two injections were done into the caudate, in the lateral and medial aspects. The depth of the injection was 15 mm and 10 µl was implanted. The syringe was withdrawn 1 mm per minute for 3 mm, then the second injection of 10 µl of the cell suspension was performed. Non-transfected SVG cells were transplanted into the putamen and SVG cells transfected with the tyrosine hydroxylase gene were transplanted into the caudate. The concentration of the cells was $2 \times 10^6$ cells per mL.

2. In addition to using implantation with the syringes with needles, cannulas of blue peek tubing connected to 22 gauge needles were constructed. The tubing was connected to 1 cc tuberculin syringes using 0 dead volume connectors. Following insertion into the target, the needle was allowed to stand for 15 minutes prior to infusion. A Harvard infusion pump holding the cell suspension was then started at 0.2 µl/min. After infusing for 15 minutes at 0.2 µl/min, the rate was increased to 0.4 µl/min and was continued for 100 minutes. After termination of the infusion, the needles were left in place for 30 minutes prior to withdrawal. The needles were then very slowly removed from the brain.

The wound was rinsed and then closed in anatomical layers. The animals woke up from the anesthesia and were transferred to their home cages 20 minutes after surgery.

EXAMPLE 3

This example demonstrates successful engraftment of the implanted SVG cells in two of the monkeys sacrificed one month following implantation. The transplanted cells were histologically healthy. There was no evidence of inflammation or tumor formation.

The brain tissue in the region of the implantations was examined as follows:

For histopathological studies animals were killed by an overdose of pentobarbital (460 mg, i.v.) and were perfused through the ascending aorta with 15 ml of ice cold phosphate-buffered saline (PBS) followed by 10% formalin. The brains were removed rapidly, cut into 6 mm coronal slices and postfixed for 30 min. in the same fixative. The tissue slices were rinsed for 48 hr. in 30% sucrose in PBS and then rapidly frozen in −70° C. Tissue was cut into 40 um coronal sections in a freezing microtome and series of sections were collected in PBS. Sections were processed for immunohistochemistry with antibodies against tyrosine hydroxylase, glial fibrillary acidic protein and T-protein. Sections adjacent to those examined for TH-IR were stained with hematoxylin and eosin. Some blocks of tissue containing implant were processed in 5 um paraffin sections and were stained as described above.

Figure 3:
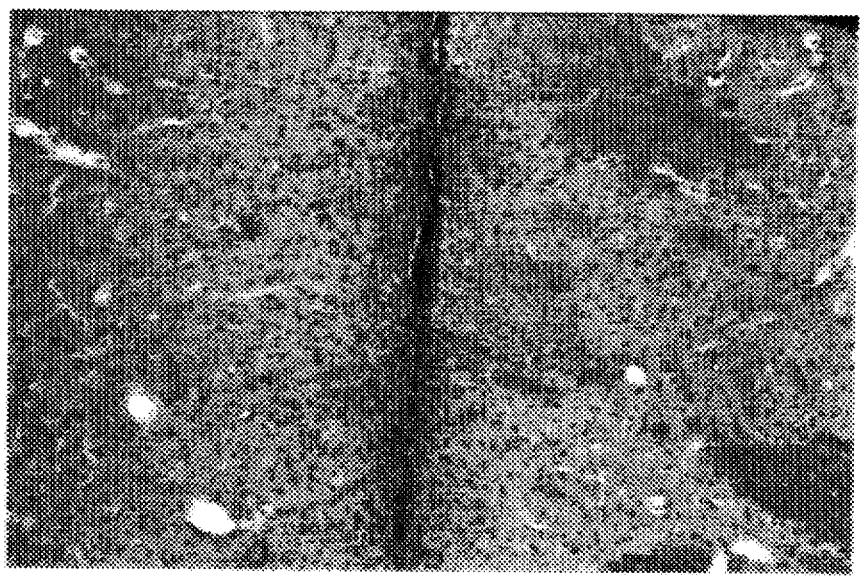
FIG. 3 demonstrates the needle track in the basal ganglia at low magnification.
Figure 4:
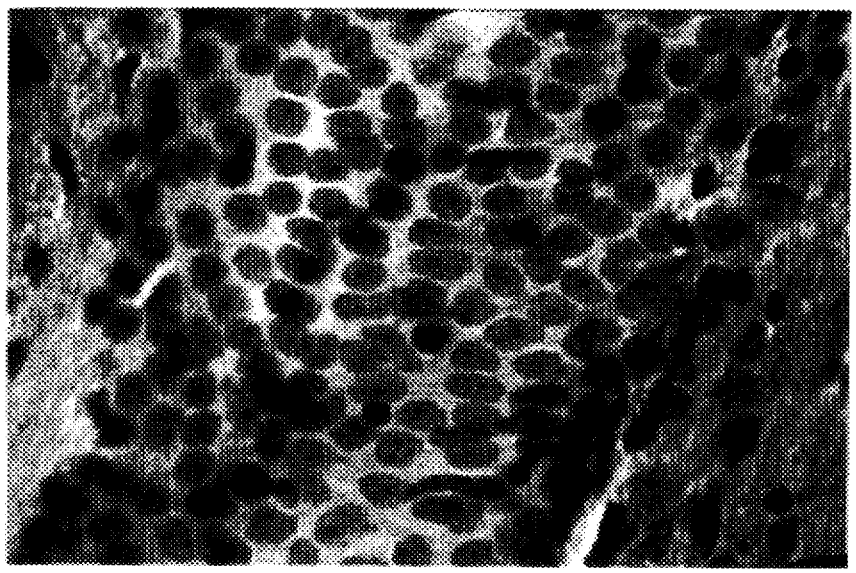
FIG. 4 illustrates a high magnification view of a needle track in the basal ganglia.
Figure 5:
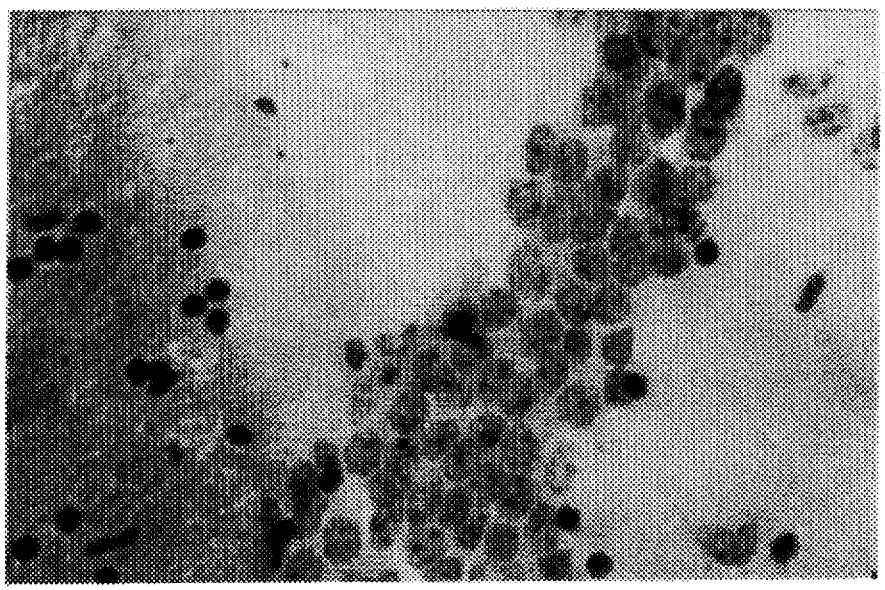
FIG. 5 demonstrates another high magnification view of a needle track in the basal ganglia.

FIG. 3 illustrates the needle track in a basal ganglia of one of the monkeys at low power. Higher power views of the needle track (FIGS. 4–5) demonstrate viable SVG cells in the track. The cells are readily identified by large nucleus containing multiple nucleoli as exhibited by SVG cells in vitro. The morphology of the implant cells is strikingly different than the morphology of surrounding cells. Inflammatory cells and tumor formation was not identified.

EXAMPLE 4

This example describes cerebral MRI evaluation one month following implantation of the four remaining monkeys. No evidence of tumor formation was present in any of the monkeys.

Figure 9:
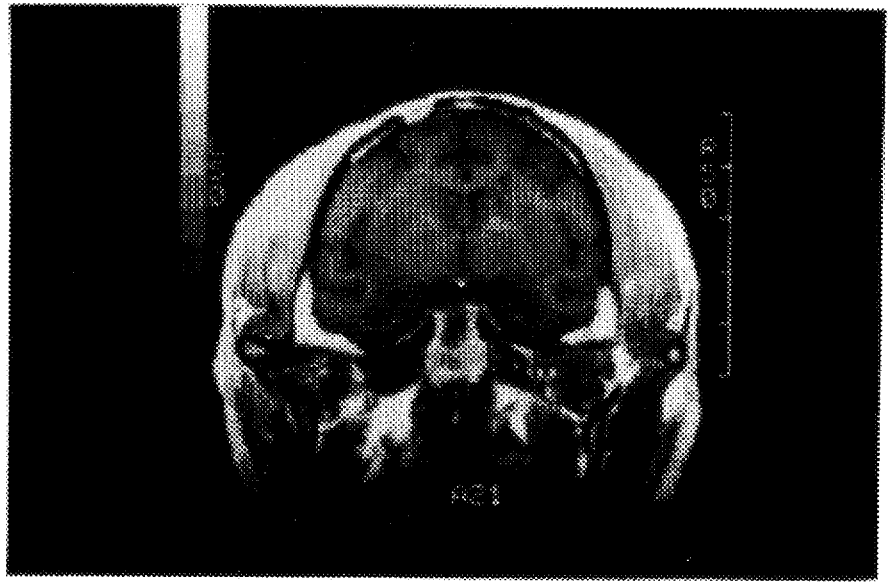
FIG. 9 demonstrates a $T_1$ weighted MRI (with gadolinium enhancement) of a monkey brain 6 months following implantation.

Following induction of anesthesia, the monkeys were placed in a standard MRI frame. $T_1$ and $T_2$ weighted images without contrast and $T_1$ weighted images with gadolinium were done using a 1.5 Tesla magnet (Signa). The scans revealed no evidence of tumor or nodule formation (FIG. 9).

EXAMPLE 5

This example demonstrates functioning of the transplanted SVG cells within the central nervous system. Host neurons migrated toward the implanted cells, neuronal dopaminergic bodies, and dopaminergic processes of host origin were extended to the implanted cells.

Two of the surviving monkeys which received SVG cell implants as described in Example 2 above were sacrificed as described. The brains were removed intact as described above and sectioned.

Figure 6:
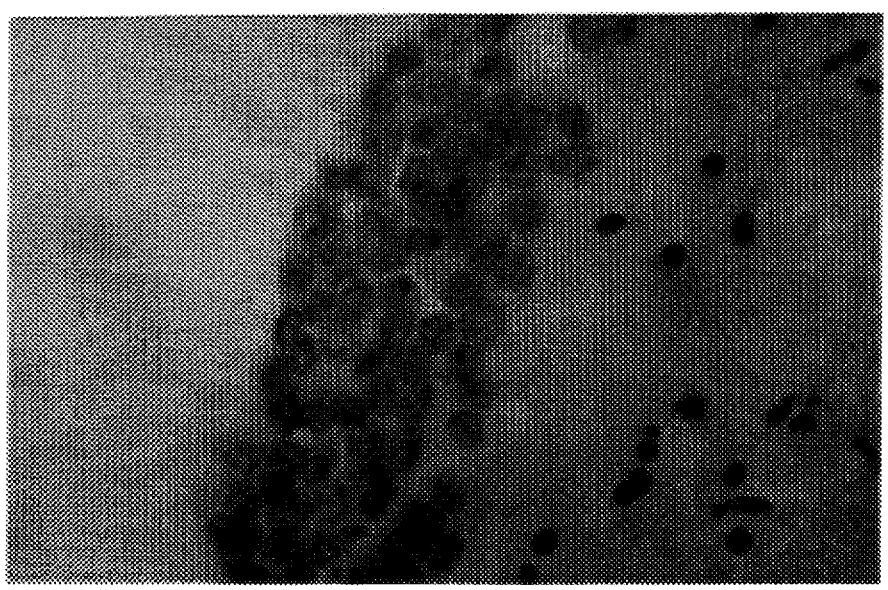
FIG. 6 demonstrates a nest of SVG cells on the wall of the lateral ventricle.
Figure 7:
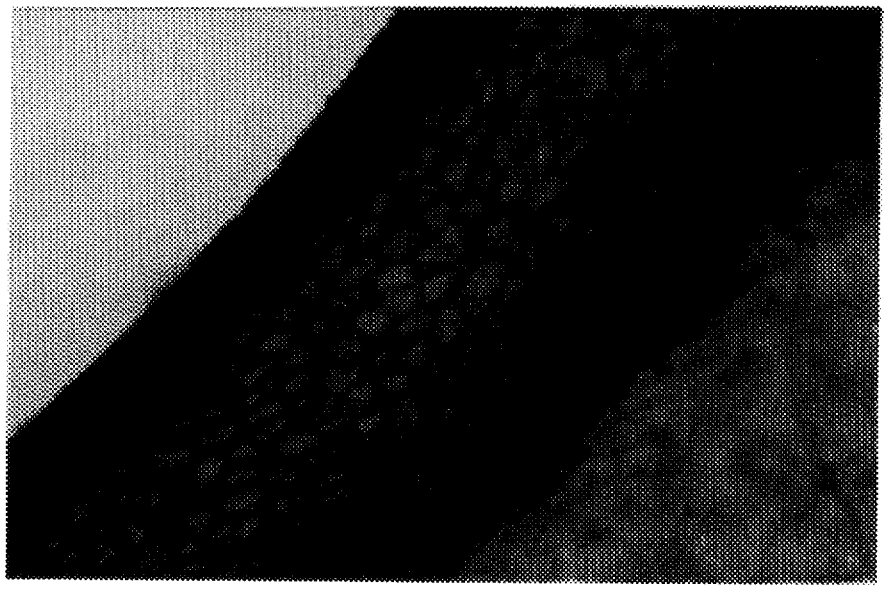
FIG. 7 illustrates implanted SVG cells on the wall of the lateral ventricle stained with an antibody to glial fibrillary acidic protein.
Figure 8:
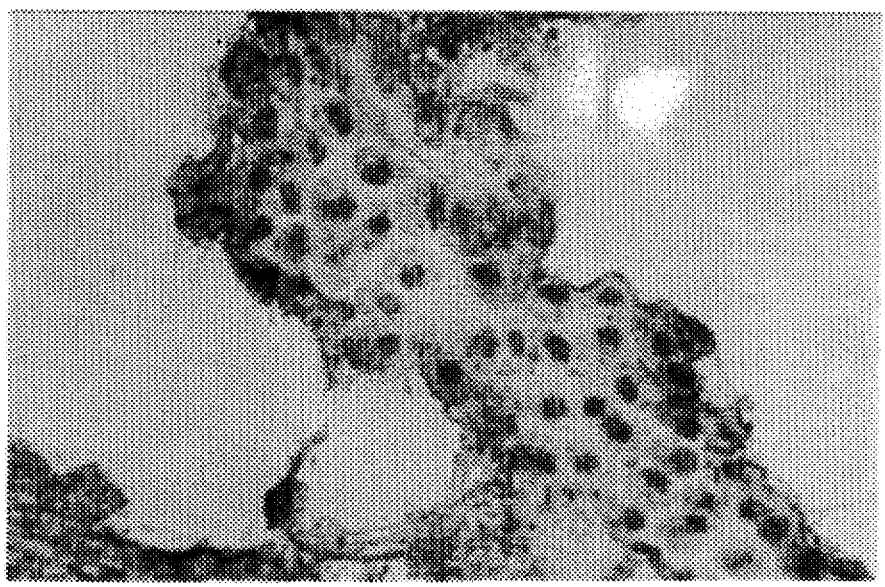
FIG. 8 demonstrates an in vivo section of implanted SVG cells stained with anti-T protein antibody.

Each section was placed on gelatin coated slides. Representative sections were stained with hematoxylin and eosin to characterize the anatomy (FIG. 6). The implanted cells exhibited characteristic SVG morphology with large nuclei having multiple nucleoli. Adjacent sections were stained with either monoclonal antibody to glial fibrillary acidic protein (GFAP), SV40 T protein, or tyrosine hydroxylase. The sections were then counterstained with hematoxylin alone. FIG. 7 illustrates an adjacent section stained with antibody to GFAP, a cytoplasmic protein of astrocytic lineage. The astrocytic origin is demonstrated by the dense cytoplasmic staining. The origin of the cells is also illustrated in FIG. 8 which clearly shows implanted cells stained with anti-T protein antibody.

Figure 10:
FIG. 10 demonstrates growth of a tyrosine hydroxylase neuron on a layer of implanted SVG cells in vivo.

The grafted cells within the caudate and putamen were viable and easily identified by anti-protein T antibody as described above. SVG cells were also identified on the wall of the lateral ventricles of all monkeys. Dopaminergic neurons exhibited neurite outgrowth toward the implanted cells (FIG. 10 demonstrates a tyrosine hydroxylase neuron stained with anti-tyrosine hydroxylase antibody in a layer of SVG cells in vivo). Dopaminergic neuronal bodies were also present in the region of the implanted SVG cells. The neurite outgrowth and presence of neuronal bodies indicate that the SVG cells produced neurotropic factors which caused neuron migration and extension of neuronal processes.

No evidence of inflammation, graft rejection, tumor or nodule formation was found in any of the sections.

EXAMPLE 6

This example describes individual encapsulation of SVG cells and preparation of the cells for implantation. The cells are encapsulated in a sodium alginate pellet.

SVG cells are grown to confluence in culture dishes. The cells are removed from the culture plates with 0.05% trypsin and 1 mM EDTA in Dulbecco's phosphate-buffered saline (PBS). The cells are suspended in PBS supplemented with $MgCl_2$, $CaCl_2$, 0.1% glucose, and 5% fetal bovine serum. Cells are collected by centrifugation, washed twice in the suspension solution as described above and centrifuged to a pellet.

The cell pellet remaining at the bottom of the centrifuge tube is resuspended in 5 mL of a 1.5% (w/v) sodium alginate solution (Keltone LV® by Kelco, Ltd., Chicago, Ill.). The alginate cell suspension is extruded into 50 mL of a 1.5% (w/v) $CaCl_2$ solution. Spherical droplets of the suspension are formed by an air jet-syringe pump droplet generator. With this apparatus, the cell-sodium-alginate suspension is extruded through a 22-gauge needle located inside a sheathed tube (3 mm I.D.) through which air flowed at a controlled rate (9 L min). As liquid droplets are forced out of the end of the needle by the syringe pump (at 20 cc hr), the droplets are pulled off by the shear forces set up by the rapidly flowing air stream. The needle tip is kept 8 cm above the surface of the $CaCl_2$ solution surface to ensure that uniform, spherical gel droplets are formed with a diameter of about 300–1000 microns.

A sample of the gelled microbeads is examined for size and shape consistency using a dissecting microscope (Wild Heerbrugg Model M8) fitted with a calibrated eye-piece. After transferring the calcium alginate gel beads, containing the immobilized cells, to a 50 mL plastic centrifuge tube with a conical bottom, the beads are washed with 30 mL each of 0.1% (w/v) CHES and 1.1% (w/v) $CaCl_2$ solutions. The supernatant volume is reduced after each washing using a vacuum aspirator. A semi-permeable capsule membrane is formed by reacting the gel droplets with an aqueous 0.05% (w/v) PLL solution (M/v of PLL=22.000) for 8 minutes. After the addition of the PLL solution, the centrifuge tube is capped and manually rocked end-to-end for the duration of the reaction to keep the capsules from sticking together. The resultant microcapsules, 300–1000 microns in diameter, are washed with 30 mL each of 0.1% CHES and 1.1% $Cacl_2$ and with two 30 mL aliquots of isotonic saline. The encapsulated cells are contacted with 30 mL of 0.03% (w/v) sodium alginate solution for 4 minutes formed an outer layer on the capsules. The interior of the microcapsules is liquified with 30 mL of a 0.05M sodium citrate solution for six minutes. The microcapsules, 400–1400 microns in diameter, are washed several times in saline to remove excess citrate and then divided into five 1 mL aliquots. Each aliquot is incubated in 10 mL DMEM medium in a 25 $cm^3$ culture flask at 37° C. in an isotemp Series 400 $CO^2$ incubator (model 413D, Fisher Scientific Co., Nepean, Ontario).

EXAMPLE 7

This example describes transfecting SVG cells with nucleic acid encoding tyrosine hydroxylase. SVG cells which expressed tyrosine hydroxylase were identified in the cultures following transfection.

A nonconfluent monolayer of SVG cells were transfected with a plasmid containing human tyrosine hydroxylase cDNA operably linked to a cytomegalovirus promoter. The cells were transfected by calcium phosphate precipitation. Two days following transfection, cells from culture were fixed and stained with a labeled antibody to tyrosine hydroxylase. Cells expressing tyrosine hydroxylase were identified.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be apparent that certain changes and modifications may be practiced within the scope of the appended claims.

What is claimed is:

1. A method for treating a mammal having a neurological syndrome or disease characterized by a dopamine deficiency comprising implanting into said mammal a therapeutically effective amount of a nontumorigenic and noninflammatory immortalized human neuro-glial cell line capable of inducing neuromigration and/or neurite extension in the mammal.

2. The method according to claim 1 wherein the immortalized human neuro-glial cell line is further characterized as anchorage dependent, not capable of growth in soft agar, not exhibiting foci formation and not expressing MHC Class II molecules.

3. The method according to claim 1 wherein the immortalized human neuro-glial cell line is derived from an immortalized human fetal cell line identifiable as ATCC CRL 8621.

4. The method as in claim 1, wherein the cell line is derived from human fetal astrocytes.

5. The method as in claim 1, wherein the cells are encapsulated by a membrane which is impermeable to antibodies.

6. The method as in claim 1, wherein the cells are implanted into the central nervous system of the mammal.

7. The method as in claim 6, wherein the cells are implanted into the basal ganglia of the mammal.

8. The method as in claim 6, wherein the cells are implanted into the lumbar theca of the mammal.

9. The method as in claim 6, wherein the cells are implanted into a lateral ventricle of the mammal.

10. A method for treating Parkinson's Disease in a mammal comprising implanting a therapeutically effective amount of a suspension of an immortalized human neuro-glial cell line having a $10^4$–$10^7$ cell density into the basal ganglia of the mammal, wherein the glial cells are characterized as nontumorigenic, noninflammatory in the recipient mammal, and capable of inducing neuromigration and/or neurite extension in the mammal.

11. The method according to claim 10 wherein the immortalized human neuro-glial cell line is further characterized as anchorage dependent, not capable of growth in soft agar, not exhibiting foci formation and not expressing MHC Class II molecules.

12. The method according to claim 10 wherein the immortalized human neuro-glial cell line is derived from an immortalized human fetal cell line identifiable as ATCC CRL 8621.

13. The method as in claim 10, wherein the mammal does not require immunosuppressive therapy following implantation of the cells.

14. A method of treating a neurological disorder characterized by a dopamine deficiency caused by a lesion in a mammal's central nervous system, comprising:

placing a needle into the central nervous system of the recipient mammal; and injecting a therapeutically effective amount of a suspension of nontumorgenic, noninflammatory and immortalized human neuro-glial cell line into the central nervous system through the needle, wherein the cell line is capable of inducing neuromigration and/or neurite extension in the mammal.

15. The method according to claim 14 wherein the immortalized human neuro-glial cell line is further characterized as anchorage dependent, not capable of growth in soft agar, not exhibiting foci formation and not expressing MHC Class II molecules.

16. The method according to claim 14 wherein the immortalized human neuro-glial cell line is derived from an immortalized human fetal cell line identifiable as ATCC CRL 8621.

17. A method as in claim 14, wherein the lesion is confined to a region of the central nervous system and the cells are injected into the region.

18. The method as in claim 14, wherein the cells are injected with a infusion pump.

19. The method according to claim 1 wherein the immortalized human neuro-glial cell line is a cell line identified as ATCC CRL 8621.

20. The method according to claim 10 wherein the immortalized human neuro-glial cell line is a cell line identified as ATCC CRL 8621.

21. The method according to claim 14 wherein the immortalized human neuro-glial cell line is a cell line identified as ATCC CRL 8621.

* * * * *